United States Patent
Du

(10) Patent No.: US 11,278,583 B2
(45) Date of Patent: Mar. 22, 2022

(54) TRADITIONAL CHINESE MEDICINE COMPOSITION FOR TREATING DISEASES CAUSED BY HUMAN PAPILLOMAVIRUS, PREPARATION METHOD AND USE THEREOF

(71) Applicant: Zhuanshe Du, Beijing (CN)

(72) Inventor: Zhuanshe Du, Beijing (CN)

(*) Notice: Subject to any disclaimer, the term of this patent is extended or adjusted under 35 U.S.C. 154(b) by 60 days.

(21) Appl. No.: 16/624,040

(22) PCT Filed: Mar. 29, 2018

(86) PCT No.: PCT/CN2018/081029
§ 371 (c)(1),
(2) Date: Dec. 18, 2019

(87) PCT Pub. No.: WO2019/183872
PCT Pub. Date: Oct. 3, 2019

(65) Prior Publication Data
US 2021/0145920 A1 May 20, 2021

(51) Int. Cl.
| | | |
|---|---|---|
| A61K 36/896 | (2006.01) | |
| A61P 31/20 | (2006.01) | |
| A61P 15/00 | (2006.01) | |
| A61K 36/288 | (2006.01) | |
| A61K 36/315 | (2006.01) | |
| A61K 36/355 | (2006.01) | |
| A61K 36/484 | (2006.01) | |
| A61K 36/489 | (2006.01) | |
| A61K 36/71 | (2006.01) | |
| A61K 36/74 | (2006.01) | |
| A61K 36/756 | (2006.01) | |

(52) U.S. Cl.
CPC ......... *A61K 36/896* (2013.01); *A61K 36/288* (2013.01); *A61K 36/315* (2013.01); *A61K 36/355* (2013.01); *A61K 36/484* (2013.01); *A61K 36/489* (2013.01); *A61K 36/71* (2013.01); *A61K 36/74* (2013.01); *A61K 36/756* (2013.01); *A61P 15/00* (2018.01); *A61P 31/20* (2018.01); *A61K 2236/331* (2013.01); *A61K 2236/333* (2013.01); *A61K 2236/51* (2013.01); *A61K 2300/00* (2013.01)

(58) Field of Classification Search
None
See application file for complete search history.

(56) References Cited

FOREIGN PATENT DOCUMENTS

| CN | 1296084 C | * | 1/2007 |
|---|---|---|---|
| CN | 101961412 A | * | 2/2011 |
| CN | 102961428 A | * | 3/2013 |
| CN | 104116860 A | * | 10/2014 |
| CN | 104147458 A | * | 11/2014 |
| CN | 105535481 A | * | 5/2016 |

OTHER PUBLICATIONS

CN-105535481-A translated (Year: 2016).*
CN-104147458-A translated (Year: 2014).*
CN-104116860-A translated (Year: 2014).*
CN-1296084-C translated (Year: 2007).*
CN-101961412-A translated (Year: 2011).*
CN-102961428-A translated (Year: 2013).*
CN-102961428-A abstract (Year: 2013).*
CN-101961412-A abstract (Year: 2011).*

* cited by examiner

*Primary Examiner* — Susan Hoffman
*Assistant Examiner* — Jacob A Boeckelman
(74) *Attorney, Agent, or Firm* — Nixon & Vanderhye P.C.

(57) ABSTRACT

The present invention discloses a traditional Chinese medicine composition for treating diseases caused by human papillomavirus, a preparation method and use thereof. The traditional Chinese medicine composition comprises: 15-60 parts of Rhizoma Smilacis Glabrae, 7.5-30 parts of *Sophora Flavescens*, 10-40 parts of Herba Hedyotidis Diffusae, 10-40 parts of Herba *Taraxaci*, 6-24 parts of Dysosma Versipellis, 7.5-30 parts of Nidus Vespae, 10-40 parts of Cortex Phellodendri, 2.5-10 parts of Fructus Bruceae, 7.5-30 parts of Fructus Cnidii, 3-12 parts of Radix Glycyrrhizae, 7.5-30 parts of Flos Lonicerae, 7.5-30 parts of Folium *Isatidis*, 5-20 parts of Radix Semiaquilegiae, and 1000-2000 parts of 75% ethanol. The traditional Chinese medicine composition has good curative effect and good safety.

4 Claims, No Drawings

TRADITIONAL CHINESE MEDICINE COMPOSITION FOR TREATING DISEASES CAUSED BY HUMAN PAPILLOMAVIRUS, PREPARATION METHOD AND USE THEREOF

This application is the U.S. national phase of International Application No. PCT/CN2018/081029 filed 29 Mar. 2018, which designated the U.S., the entire contents of which is hereby incorporated by reference.

TECHNICAL FIELD

The present invention belongs to the field of medicine, and particularly relates to a traditional Chinese medicine composition for treating diseases caused by human papillomavirus, a preparation method and use thereof.

BACKGROUND OF RELATED ART

Human papillomavirus (HPV) is an epithelial virus that is a member of the genus A of the Papoviruidae family It is a small DNA virus that infects the epidermis and mucosal squamous epithelium. It is 52-55 nm in diameter and has no capsule. It has a regular icosahedral structure with 72 shells on the surface, and the viral genome is a double-stranded circular DNA molecule, which is widely distributed in humans and has a high degree of specificity. HPV has been found to have more than 100 subtypes. Low-risk HPV can cause a variety of benign lesions in the mucous membranes of the skin, such as condyloma *acuminatum* and skin warts. High-risk HPV is the primary cause of cervical carcinoma. Cervical carcinoma is one of the most common gynecologic malignancies in developing countries.

Condyloma *acuminatum* (known as "SAO warts" or "SAO verrucas" in Chinese medicine), common warts, etc., are all kind of benign skin tumors produced by human papillomavirus (HPV) through the skin's mucous membrane infection caused by the subtle damage of the human body through an incubation period of 3 to 5 months. Condyloma *acuminatum*, also known as spiky wet warts, genital warts, and sexually transmitted warts, can cause common infectious diseases characterized with verrucous vegetations at the places of genitalia, anus etc., which occurs mostly around the genitals and anus of men and women. Generally, it is a papule with a needle tip size at the beginning, which is light red, dark red or dirty gray, and then develops into a papillary ridge, which merges or overlaps each other, like cauliflower, moist and soft, and often accompanied by varying degrees of itching.

In recent years, the high incidence of cervical carcinoma is seriously threatening the health and life of women. Only by effectively removing HPV can we effectively prevent the occurrence of cervical carcinoma. Modern medicine for the prevention of cervical HPV infection is vaccination, but the scope is limited, expensive, and need repeated injections. There is currently no effective means of infecting HPV. Injection of interferon is difficult to promote, since it has toxic and side effects, and with long course of treatment and low cure rate.

With the deepening of clinical research, some drugs for treating the above-mentioned diseases caused by human papillomavirus have appeared in the market Some of the existing drugs belong to the palliative, some use expensive components, and some are discontinued due to inaccurate efficacy during the application process.

Skin tinea is a contagious skin disease. The skin has red rash or small red plaque. The more scratches, the skin will be more red itchy. The symptoms of skin tinea can be single, or several pieces, and merge with each other. The affected area often appears in places with more sweating, such as the feet, the inner thighs, etc., can also occur in the trunk and limbs, occurs less on the face, and the performance is often atypical, long-term skin lesions can be dark red, with thin scales on it, and local hyperpigmentation. Dermatophytosis is a common and frequently-occurring disease, second to dermatitis and eczema, and in the first place in infectious skin diseases.

The information disclosed in background part is only intended to enhance an understanding of the general background of the invention, and should not be taken as an acknowledgement or any form of suggestion that this information forms the prior art already known to a person skilled in the art.

SUMMARY OF THE INVENTION

The object of the present invention is to provide a traditional Chinese medicine composition, preparation method and use thereof, wherein the traditional Chinese medicine composition can effectively treat diseases caused by human papillomavirus, has good druggability, and has good curative effect and safety.

To achieve the above object, the present invention provides a traditional Chinese medicine composition comprising the following pharmaceutical ingredients in parts by weight: 15-60 parts of Rhizoma Smilacis Glabrae, 7.5-30 parts of *Sophora Flavescens*, 10-40 parts of Herba Hedyotidis Diffusae, 10-40 parts of Herba *Taraxaci*, 6-24 parts of Dysosma Versipellis, 7.5-30 parts of Nidus Vespae, 10-40 parts of Cortex Phellodendri, 2.5-10 parts of Fructus Bruceae, 7.5-30 parts of Fructus Cnidii, 3-12 parts of Radix Glycyrrhizae, 7.5-30 parts of Flos Lonicerae, 7.5-30 parts of Folium *Isatidis*, 5-20 parts of Radix Semiaquilegiae, and 1000-2000 parts of 75% ethanol.

In the above traditional Chinese medicine composition, the main drug is Rhizoma Smilacis Glabrae that tastes sweet and light. The Rhizoma Smilacis Glabrae has the effects of dehumidification, heat removal and detoxification. It can treat a variety of sexually transmitted diseases, such as syphilis and gonorrhea, etc., which is the monarch drug in the prescription.

The secondary main drugs include the following features:

*Sophora Flavescens* tastes slightly bitter, cold in property, which has the effects of clearing away heat and drying dampness, killing insects and promoting urination. It can cure gonorrhea, pruritus vulvae, cervical erosion and other diseases.

Herba Hedyotidis Diffusae tastes bitter and sweet, cold in property, which can be used for clearing away heat and detoxification, removing dampness and smooth showering, as well as anti-tumor. It can be used for sore swollen poison, sore, tumor, and urinary tract infection.

Herba *Taraxaci* tastes sweet and bitter, slightly cold in property, which has the effects of heat removal and detoxification, damp-inhibiting and wind-dispersing, and promoting diuresis and relieving stranguria. It can be used for sore swollen poison, erysipelas, eczema and other diseases.

Dysosma Versipellis tastes slightly spicy, cool in property, which has the effects of heat removal and detoxification, as well as scattered carbuncle swelling, and can treat carbuncle, erysipelas and other diseases.

Nidus Vespae tastes bitter and salty, flat in property, which has the effects of dispelling wind and counteracting toxic substances, killing insects and stopping carbuncle, and can treat symptoms such as malignant sores, tumors, rash and pruritus.

Cortex Phellodendri tastes bitter, cold in property, which has the effects of clearing away heat and drying dampness, purging fire and clearing hectic heat, detoxification treatment of sores, and can treat vaginal itch, sore swollen poison, eczema, wet sores and other symptoms.

Flos Lonicerae tastes sweet, cold in property, which has the effects of heat removal and detoxification, cool and windy heat, and can be used for swollen welling-abscess and clove sores, throat impediment, erysipelas, heat toxin and bloody flux.

Folium *Isatidis* tastes bitter, cold in property, which has the effects of heat removal and detoxification, cooling blood and eliminating spots, and is used for swelling, throat impediment, erysipelas and other symptoms.

Radix semiaquilegiae tastes sweet and bitter, cold in property, which has the effects of heat removal and detoxification, reducing swelling and dispersing, and is used for swollen welling-abscess and clove sores, mammary abscess, scrofula, snake bites and other symptoms.

The above nine drugs assists the main drug, and have the effects of clearing heat, dehumidifying and detoxifying, together called secondary main drugs.

Assistant Drugs:

Fructus Bruceae tastes bitter, cold in property, and has a small poison. It has the effects of heat removal and detoxification, killing insects and corroding warts. It is often used for wart and corn (external use), skin cancer, vaginitis and other diseases.

Fructus Cnidii tastes spicy and bitter, warm in property, which has the effects of dispelling wind and drying dampness, and killing parasites to relieve itching. It can be used for skin eczema, scrotum wet itching, female pruritus and other diseases.

The above two drugs are used as assistant drugs to assist the monarch drug to dry the dampness and kill the insects, and corrupt warts. Fructus Cnidii has warm property which can also make the heat-clearing medicine bitter and cold, which can play an opposite and complementary role.

Conductant Drug:

Radix Glycyrrhizae tastes sweet, flat in property, which can clear away heat and detoxification, slowly stop warts, and can solve the poison of 100 drugs, which is the conductant drug in the prescription.

The whole prescription has a total of 13 drugs, and the monarch drug, minister drug, assistant drug and conductant drug are clearly demarcated, which have synergistic effect between each other.

In another embodiment, the traditional Chinese medicine composition comprises the following pharmaceutical ingredients in parts by weight: 38 parts of Rhizoma Smilacis Glabrae, 19 parts of *Sophora Flavescens*, 30 parts of Herba Hedyotidis Diffusae, 30 parts of Herba *Taraxaci*, 15 parts of Dysosma Versipellis, 19 parts of Nidus Vespae, 30 parts of Cortex Phellodendri, 6 parts of Fructus Bruceae, 19 parts of Fructus Cnidii, 7 parts of Radix Glycyrrhizae, 19 parts of Flos Lonicerae, 19 parts of Folium *Isatidis*, 13 parts of Radix Semiaquilegiae, and 1500 parts of 75% ethanol.

In another embodiment, the traditional Chinese medicine composition is a tincture.

The invention also provides a preparation method of the traditional Chinese medicine composition, the preparation method comprising the following steps:

(1) Soaking 13-17 parts of Dysosma Versipellis, 17-21 parts of Nidus Vespae, 4-8 parts of Fructus Bruceae, 17-21 parts of Flos Lonicerae, and 11-15 parts of Radix Semiaquilegiae in 95% ethanol for 8-12 days, taking a first supernatant and ethanol extracting and concentrating the first supernatant at 60-70° C., 0.02-0.05 MPa to obtain an ethanol extract concentrate.

(2) Adding 1400-2500 parts of ionized water to 36-40 parts of Rhizoma Smilacis Glabrae, 17-21 parts of *Sophora Flavescens*, 28-32 parts of Herba Hedyotidis Diffusae, 28-32 parts of Herba *Taraxaci*, 28-32 parts of Cortex Phellodendri, 17-21 parts of Fructus Cnidii, 5-9 parts of Radix Glycyrrhizae, and 17-21 parts of Folium *Isatidis*, heating and boiling, and taking out the filtrate to obtain a water extract.

(3) Mixing the ethanol extract concentrate with the water extract, filtering out a second supernatant, and adding 30% ethanol to get 700-800 parts of the traditional Chinese medicine composition.

Preferably, the preparation method comprises the following steps:

(1) Soaking 15 parts of Dysosma Versipellis, 19 parts of Nidus Vespae, 6 parts of Fructus Bruceae, 19 parts of Flos Lonicerae, and 13 parts of Radix Semiaquilegiae in 95% ethanol for 10 days, taking a first supernatant, ethanol extracting and concentrating the first supernatant at 65° C., 0.04 MPa to obtain an ethanol extract concentrate;

(2) Adding 1920 parts of ionized water to 38 parts of Rhizoma Smilacis Glabrae, 19 parts of *Sophora Flavescens*, 30 parts of Herba Hedyotidis Diffusae, 30 parts of Herba *Taraxaci*, 30 parts of Cortex Phellodendri, 19 parts of Fructus Cnidii, 7 parts of Radix Glycyrrhizae, and 19 parts of Folium *Isatidis*, heating and boiling, and taking the filtrate to obtain a water extract; and (3) Mixing the ethanol extract concentrate with the water extract, filtering the supernatant, and adding 30% ethanol to get 750 parts of the traditional Chinese medicine composition.

In another embodiment, the specific gravity of the prepared traditional Chinese medicine composition is 0.90-1.10.

In the other embodiment, the specific gravity of the traditional Chinese medicine composition is measured by a Baume's specific gravity meter.

In another embodiment, the specific gravity of the prepared traditional Chinese medicine composition is 0.92-1.12.

The invention also provides the use of the above traditional Chinese medicine composition for preparing a medicament for preventing and/or treating condyloma *acuminatum*.

The invention also provides the use of the above traditional Chinese medicine composition for preparing a medicament for preventing and/or treating cervical precancerous lesions.

The present invention also provides the use of the above traditional Chinese medicine composition for the preparation of a medicament for preventing and/or treating skin tinea.

Compared with the prior art, the present invention has the following beneficial effects: the pharmaceutical composition of the present invention can effectively inhibit the replication of human papillomavirus nucleic acid, thereby effectively treating condyloma *acuminatum* caused by human papillomavirus, cervical HPV infection and cervical precancerous lesions caused by HPV infection, as well as pathogens of the skin tinea. The pharmaceutical composition has the effect of clearing away heat and removing toxic substances. In addition, it has the simple preparation method, good curative effect and good safety.

DETAILED DESCRIPTION OF THE EMBODIMENTS

The present invention is further illustrated by the following examples, but it should be understood that the scope of the invention is not limited by the specific embodiments.

Example 1 Composition and Preparation Method of Traditional Chinese Medicine Composition Composition:

38 parts by weight of Rhizoma Smilacis Glabrae, 19 parts of *Sophora Flavescens,* 30 parts of Herba Hedyotidis Diffusae, 30 parts of Herba *Taraxaci,* 15 parts of Dysosma Versipellis, 19 parts of Nidus Vespae, 30 parts of Cortex Phellodendri, 6 parts of Fructus Bruceae, 19 parts of Fructus Cnidii, Radix 7 parts of Glycyrrhizae, 19 parts of Flos Lonicerae, 19 parts of Folium *Isatidis,* 13 parts of Radix Semiaquilegiae, 1500 parts of 75% ethanol.

The preparation method is as follows.

(1) soaking 15 parts of Dysosma Versipellis, 19 parts of Nidus Vespae, 6 parts of Fructus Bruceae, 19 parts of Flos Lonicerae, and 13 parts of Radix semiaquilegiae in 95% ethanol for 10 days, taking a first supernatant of the above soaked solution. Then the first supernatant is extracted using ethanol, and then the first supernatant is concentrated at 65° C., 0.04 MPa, to obtain an ethanol extract concentrate.

(2) adding 1920 parts of ionized water to 38 parts of Rhizoma Smilacis Glabrae, 19 parts *Sophora Flavescens,* 30 parts Herba Hedyotidis Diffusae, 30 parts Herba *Taraxaci,* 30 parts of Cortex Phellodendri, 19 parts Fructus Cnidii, 7 parts of Radix Glycyrrhizae, and 19 parts of Folium *Isatidis,* heating and boiling, and taking out the filtrate to obtain a water extract.

(3) mixing the ethanol extract concentrate with the water extract, filtering out a second supernatant from the above mixed solution, and adding 30% ethanol to get 750 parts of the composition.

The prepared Chinese medicine composition is measured to by a Baume's specific gravity meter obtain a specific gravity of 0.968.

Example 2 Inhibition of Human Papillomavirus Nucleic Acid Replication In Vitro by the Traditional Chinese Medicine Composition of the Present Application First, 30 samples of genital condyloma *acuminatum* are collected, and Human papillomavirus (HPV) nucleic acid DNA after homogenization is collected.

Secondly, the traditional Chinese medicine composition prepared in Example 1 is selected, and the composition is mixed with water to make diluted solutions with concentration of 5%, 2.5%, 1.25%, 0.625%, and 0.3125%. The samples are immersed in the solution for 34 hours and 58 hours respectively. The test temperature is 25° C. Saline is used as a negative control.

The Conclusion is as follows:

When immersed for 34 hours: no nucleic acid was detected when the concentration of the traditional Chinese medicine composition of the present invention ≥2.5%; 6.67% of the nucleic acid was detected at the concentration of 1.25%; 50% of the nucleic acid was detected at the concentration of 0.625%; 93.33% of the nucleic acid was detected at the concentration of 0.3125%;

When immersed for 58 hours: no nucleic acid was detected when the concentration of the traditional Chinese medicine composition of the present invention ≥1.25%; 26.67% of the nucleic acid was detected at the concentration of 0.625%; and 96.673% of the nucleic acid was detected at the concentration of 0.3125%;

Saline control group: 100% of nucleic acid was detected after 34 hours and 58 hours.

It is proved that the traditional Chinese medicine composition of the present embodiment can inhibit the replication of human papillomavirus nucleic acid in vitro, effectively destroy the viral DNA, has the ability to kill the virus, and the inhibition of HPV is strengthened with the prolongation of time and the increase of concentration, The minimum effective concentration is 1.25%.

Example 3 the Traditional Chinese Medicine Composition of the Present Application Treats Condyloma *acuminatum*

1. Firstly, 18-65 years old male and female genital condyloma *acuminatum* cases were chosen: single wart diameter <0.5 cm, wart numbers <5 (wart mass diameter <1 cm), the wart was located in the external or perianal part. The cases were divided into the test group and the control group, 30 persons each, the test group used the traditional Chinese medicine composition prepared in Example 1 of the present invention, and the control group used the imiquimod cream.

The following patients are excluded: skin disease patients with impact assessment; severe liver and kidney dysfunction; those who were allergic to imiquimod cream; those who received viral therapy.

2. Test Method:

Test group: The pharmaceutical composition prepared in Example 1 of the present invention was taken out with a cotton swab and applied to the warts and the surrounding 2 cm area. 2 times/day, continuous use for 3 days, stopped for 4 days, 7 days for a course of treatment. If the wart was not completely detached after the end of a course of treatment, a second course of treatment could be used for up to four courses of treatment.

Control group: 5% imiquimod cream was applied to the warts and the surrounding 2 cm area with a cotton swab three times a week, every other day for 8 weeks.

The two groups of patients were re-examined every 2 weeks for 8 weeks. The curative effect was observed and samples were collected for viral marker detection by PQ-PCR.

3. Results

The subjects were actually completed in 60 cases, 30 cases in the test group, and 30 cases in the control group.

3.1 Complete Shedding Rate of Warts in the First Course of Treatment

TABLE 1

Comparison of complete shedding rate of warts in the first course of treatment of two different drugs

| | Effective number of people in the first course of treatment | Invalid number of people in the first course of treatment | Total |
|---|---|---|---|
| Test group | 26 | 4 | 30 |
| Control group | 18 | 12 | 30 |

Note:
$\chi^2 = 5.455$
$p = 0.020$ 3.2 Virus Negatve Detection

TABLE 2

Comparison of the negative rate of HPV virus markers after treatment with two drugs

|  | Trans-negative number | Invalid number | Total |
| --- | --- | --- | --- |
| Test group | 28 | 2 | 30 |
| Control group | 20 | 10 | 30 |

Note:
$\chi^2 = 6.670$
$p = 0.010$ 3.3: Recurrence Statistics

TABLE 3

Comparison of recurrence rate after treatment with two drugs

|  | Number of recurrence | Number of non-recurrence | Total |
| --- | --- | --- | --- |
| Test group | 1 | 27 | 28 |
| Control group | 5 | 15 | 20 |

Note:
$\chi^2 = 4.898$
$p = 0.027$

Conclusion: After the first course of treatment with different drug treatments in the test group and the control group, the complete shedding rate of warts, the recurrence rate of cases and the negative rate of HPV virus markers are counted. The comparison results showed that the traditional Chinese medicine composition prepared in Example 1 of the present invention has a remarkable effect on treating condyloma *acuminata*, and the course of treatment is short (7 days), and the HPV virus markers have a high negative rate and a low recurrence rate.

Example 4 the Traditional Chinese Medicine Composition of the Present Application Acts on Cervical HPV Infection and HPV-Induced Cervical Intraepithelial Neoplasia 1. After the confirmation from the hospital outpatients, the test from liquid-based ultrathin (TCT), colposcopy and histopathological examination, the pathological results were confirmed as one of the following conditions: cervical HPV-positive, cervical intraepithelial neoplasia (CIN1, CIN2).

2 Treatment Methods

All of them were treated in non-menstrual period. The sterilized cotton balls with tail line were used to take 1~2 ml of the traditional Chinese medicine composition prepared in Example 1 of the present invention, which was applied to the cervix, and was taken out by the patient for about 1-3 hours, 1 time/d, used 3d for a while, rest for 4d, and used 4 courses of the treatment. Reviewed after deactivation.

3 Efficacy Criteria
3.1 HPV Infection
  (1) Cure: HPV DNA review results were negative.
  (2) Invalid: HPV DNA review results were positive.
3.2 CIN Cure:
  (1) Both TCT and HPV tests were negative. Colposcopy, it was also valid if there was no abnormality under the microscope or confirmed by biopsy to confirm the absence of CIN.
  (2) Invalid: pathological diagnosis after biopsy CIN1 or CIN2 remained unchanged.

3.3 The $\chi^2$ test was used for statistical analysis. $P<0.05$ was considered statistically significant.

4. Results

TABLE 4

Traditional Chinese medicine composition of the present invention acts on cervical HPV infection and cervical intraepithelial neoplasia

| Diseases | Number of cases | Valid | Invalid |
| --- | --- | --- | --- |
| Cervical HPV positive | 34 | 21 | 13 |
| C1N1 | 7 | 6 | 1 |
| C1N2 | 4 | 3 | 1 |

Conclusion: The traditional Chinese medicine composition prepared in Example 1 of the present invention has significant effects on cervical HPV infection and HPV-induced cervical intraepithelial neoplasia.

Example 5 the Traditional Chinese Medicine Composition of the Present Application Acts on Pathogens of the Skin Tinea The two most common pathogens, *Trichophyton rubrum* and *Candida albicans*, were conducted pre-experiments of the external drug sensitivity by using M-38 A2 (skin sputum) and M27-A3 (yeast) micro-liquid dilution method developed by CLSI experiment.

1 Test Strains

The pre-experimental strains include 1 strain of *Trichophyton rubrum* (BMU-08583) and 1 strain of *Candida albicans* (BMU-05260).

2 External Drug Sensitivity Test Method

*Trichophyton rubrum* and *Trichophyton* rubrum were measured by the M38-A2 micro-liquid dilution method established by CLSI; *Candida albicans* was measured by the M27-A3 micro-liquid dilution method established by CLSI.

3 Result Judgment

The results were interpreted in accordance with the standards established by CLSI. Only when the growth control grew well, the test was considered successful and the results could be interpreted.

4 Results 4.1 Pre-Experimental Results for *Trichophyton rubrum* and *Candida albicans*

The minimum inhibitory concentration (MIC) of the traditional Chinese medicine composition prepared in Example 1 of the present invention against *Candida albicans* was 1:8; the MIC against *Trichophyton rubrum* was 1:128. The MIC of the traditional Chinese medicine composition prepared in Example 1 of the present invention for removing the ethanol stock solution against *Candida albicans* was 1:8; the MIC for the *Trichophyton rubrum* was 1:128. The pre-experimental results of the external drug sensitivity of the traditional Chinese medicine composition prepared in Example 1 of the present invention were shown in Table 5.

TABLE 5

Results of external drug sensitivity test of traditional
Chinese medicine composition of the present invention

| Strains | Traditional Chinese medicine composition containing ethanol MIC | Traditional Chinese medicine composition without ethanol MIC |
|---|---|---|
| Candida albicans (1) | 1:8 | 1:8 |
| Trichophyton rubrum (1) | 1:128 | 1:128 |

The experimental results suggested that the traditional Chinese medicine composition of the present invention has certain antifungal activity in vitro, especially for the *Trichophyton rubrum*, and the MIC is 1:128 (that is, the result of diluting the original solution of the Chinese medicine composition by 8 times). It also has antibacterial activity against *Candida albicans*, and the MIC is 1:8 (i.e., the result of diluting the original solution of the Chinese medicine composition by 4 times). The results showed that the traditional Chinese medicine composition containing and without the ethanol solution has no effect on the results of the external drug sensitivity test, indicating that the ethanol has no antifungal activity, and the true antifungal activity comes from the traditional Chinese medicine ingredients in the traditional Chinese medicine composition of the present invention.

4.2 Results of External Antibacterial Activity Against *Trichophyton rubrum* and Toe (Finger) *Trichophyton*

The MIC of the traditional Chinese medicine composition prepared in Example 1 of the present invention against *Trichophyton rubrum* was 1:64 to 1:256; the MIC of toe (finger) *Trichophyton* was 1:64 to 1:128. The consistency of the results of the two tests per strain was very good. The results of external antibacterial activity against *Trichophyton rubrum* and toe (finger) *Trichophyton* were shown in Table 6.

TABLE 6

Results of external antibacterial activity of the traditional
Chinese medicine composition against dermatophytes

| Strains | 1:32 | 1:64 | 1:128 | 1:256 | 1:512 |
|---|---|---|---|---|---|
| Trichophyton rubrum | 10 | 0 | 4 | 4 | 2 | 0 |
| toe (finger) Trichophyton | 10 | 0 | 7 | 3 | 0 | 0 |
| Total | 20 | 0 | 11 | 7 | 2 | 0 |

The traditional Chinese medicine composition prepared in Example 1 of the present invention has obvious antifungal activity to *Trichophyton rubrum* and Toe (finger) *Trichophyton*, and the MIC of *Trichophyton rubrum* is 1:64-1:256. That is, the stock solution of the traditional Chinese medicine composition of the present invention has an antifungal effect when diluted to 7 to 9 times; the MIC of the toe (referring to) *Trichophyton* is 1:64 to 1:128, that is, the stock solution of the traditional Chinese medicine composition of the present application has an antifungal effect when diluted to 7 to 8 times.

Example 6

Composition

Rhizoma Smilacis Glabrae 38 parts, *Sophora Flavescens* 19 parts, Herba Hedyotidis Diffusae 30 parts, Herba Taraxaci 30 parts, Dysosma Versipellis 15 parts, Nidus Vespae 19 parts, Cortex Phellodendri 30 parts, Fructus Bruceae 6 parts, Fructus Cnidii 19 parts, Radix Glycyrrhizae 7 parts, Flos Lonicerae 19 parts, Folium *Isatidis* 19 parts, Radix Semiaquilegiae 13 parts, *Bassia hyssopifolia* 12 parts, 75% ethanol 1500 parts.

Preparation Method (1) soaking 15 parts of Dysosma Versipellis, 19 parts of Nidus Vespae, 6 parts of Fructus Bruceae, 19 parts of Flos Lonicerae, and 13 parts of Radix semiaquilegiae in 95% ethanol for 10 days, taking out a first supernatant, ethanol-extracting the first supernatant, and concentrating the first supernatant at 65° C., 0.04 MPa to obtain an ethanol extract concentrate.

(2) adding 1920 parts of ionized water into 38 parts of Rhizoma Smilacis Glabrae, 19 parts *Sophora Flavescens*, 30 parts Herba Hedyotidis Diffusae, 12 parts of *Bassia hyssopifolia*, 30 parts Herba *Taraxaci*, 30 parts of Cortex Phellodendri, 19 parts Fructus Cnidii, 7 parts of Radix Glycyrrhizae, and 19 parts of Folium *Isatidis*, heating and boiling, and taking out the filtrate to obtain a water extract; and (3) mixing the ethanol extract concentrate with the water extract, filtering out a second supernatant, and adding 30% ethanol into the second supernatant to get 750 parts of the. The Traditional Chinese Medicine Composition of the Present Invention Acts on Cervical HPV Infection and HPV-Induced Cervical Intraepithelial Neoplasia 1. After the confirmation from the hospital outpatients, the test from liquid-based ultrathin (TCT), colposcopy and histopathological examination, the pathological results were confirmed as one of the following conditions: cervical HPV-positive, cervical intraepithelial neoplasia (CIN1, CIN2).

2 Treatment Methods

All of them were treated in non-menstrual period. The sterilized cotton balls with tail line were used to take 1~2 ml of the traditional Chinese medicine composition prepared in Example 1 of the present invention, which was applied to the cervix, and was taken out by the patient for about 1-3 hours, 1 time/d, used 3d for a while, rest for 4d, and used 4 courses of the treatment. Reviewed after deactivation.

3 Efficacy Criteria 3. 1 HPV Infection (1) Cure: HPV DNA review results were negative.

(2) Invalid: HPV DNA review results were positive.

3.2 CIN Cure:

(1) Both TCT and HPV tests were negative. Colposcopy, it was also valid if there was no abnormality under the microscope or confirmed by biopsy to confirm the absence of CIN.

(2) Invalid: pathological diagnosis after biopsy CIN1 or CIN2 remained unchanged.

3.3 The $\chi 2$ test was used for statistical analysis. P<0.05 was considered statistically significant.

4. Results

TABLE 7

Traditional Chinese medicine composition of the present invention acts
on cervical HPV infection and cervical intraepithelial neoplasia

| Diseases | Number of cases | Valid | Invalid |
|---|---|---|---|
| Cervical HPV positive | 34 | 30 | 4 |
| C1N1 | 7 | 7 | 0 |
| C1N2 | 4 | 4 | 0 |

Conclusion: The traditional Chinese medicine composition prepared in Example 6 of the present invention has significant effects on cervical HPV infection and HPV-induced cervical intraepithelial neoplasia.

The experimental effect of the present embodiment is obviously superior to the experimental effect of the composition of Example 1. Compared with Example 1, the other conditions are exactly the same, only the *Bassia hyssopifolia* is added, it can be seen that *Bassia hyssopifolia* has the effect of treating cervical HPV infection and HPV-induced cervical intraepithelial neoplasia.

Example 7

Composition

Rhizoma Smilacis Glabrae 38 parts, *Sophora Flavescens* 19 parts, Herba Hedyotidis Diffusae 30 parts, Herba *Taraxaci* 30 parts, Dysosma Versipellis 15 parts, Nidus Vespae 19 parts, Cortex Phellodendri 30 parts, Fructus Bruceae 6 parts, Fructus Cnidii 19 parts, Radix Glycyrrhizae 7 parts, Flos Lonicerae 19 parts, Folium *Isatidis* 19 parts, Radix Semiaquilegiae 13 parts, Fauriella 18 parts, 75% ethanol 1500 parts.

Preparation Method (1) soaking 15 parts of Dysosma Versipellis, 19 parts of Nidus Vespae, 6 parts of Fructus Bruceae, 19 parts of Flos Lonicerae, 13 parts of Radix semiaquilegiae and 18 parts of Fauriella in 95% ethanol for 10 days, taking the supernatant, and ethanol extracting and concentrating the supernatant at 65° C., 0.04 MPa to obtain an ethanol extract concentrate;

(2) adding 1920 parts of ionized water into 38 parts of Rhizoma Smilacis Glabrae, 19 parts *Sophora Flavescens*, 30 parts Herba Hedyotidis Diffusae, 30 parts Herba *Taraxaci*, 30 parts of Cortex Phellodendri, 19 parts Fructus Cnidii, 7 parts of Radix Glycyrrhizae, and 19 parts of Folium *Isatidis*, heating and boiling, and taking the filtrate to obtain a water extract; and (3) mixing the ethanol extract concentrate with the water extract, filtering out a second supernatant, and adding 30% ethanol into the second supernatant to get 750 parts of traditional Chinese medicine composition.

The traditional Chinese medicine composition of the present embodiment acts on pathogens of the skin tinea.

The two most common pathogens, *Trichophyton rubrum* and *Candida albicans*, were conducted pre-experiments of the external drug sensitivity by using M-38 A2 (skin sputum) and M27-A3 (yeast) micro-liquid dilution method developed by CLSI experiment.

1 Test Strains

The pre-experimental strains include 1 strain of *Trichophyton rubrum* (BMU-08583) and 1 strain of *Candida albicans* (BMU-05260).

2 External Drug Sensitivity Test Method

*Trichophyton rubrum* and *Trichophyton rubrum* were measured by the M38-A2 micro-liquid dilution method established by CLSI; *Candida albicans* was measured by the M27-A3 micro-liquid dilution method established by CLSI.

3 Result Judgment

The results were interpreted in accordance with the standards established by CLSI. Only when the growth control grew well, the test was considered successful and the results could be interpreted.

4 Results 4.1 Pre-Experimental Results for *Trichophyton rubrum* and *Candida albicans*

The minimum inhibitory concentration (MIC) of the traditional Chinese medicine composition prepared in Example 6 of the present invention against *Candida albicans* was 1:64; the MIC against *Trichophyton rubrum* was 1:256. The MIC of the traditional Chinese medicine composition prepared in Example 1 of the present invention for removing the ethanol stock solution against *Candida albicans* was 1:64; the MIC for the *Trichophyton rubrum* was 1:256. The pre-experimental results of the external drug sensitivity of the traditional Chinese medicine composition prepared in Example 1 of the present invention were shown in Table 8.

TABLE 8

Results of external drug sensitivity test of traditional Chinese medicine composition of the present invention

| Strains | Traditional Chinese medicine composition containing ethanol MIC | Traditional Chinese medicine composition without ethanol MIC |
| --- | --- | --- |
| Candida albicans (1) | 1:64 | 1:64 |
| Trichophyton rubrum (1) | 1:256 | 1:256 |

The experimental results suggested that the traditional Chinese medicine composition of the present invention has certain antifungal activity in vitro, especially for the *Trichophyton rubrum*, and the MIC is 1:256. It also has antibacterial activity against *Candida albicans*, and the MIC is 1:64. The results showed that the traditional Chinese medicine composition containing and without the ethanol solution has no effect on the results of the external drug sensitivity test, indicating that the ethanol has no antifungal activity, and the true antifungal activity comes from the traditional Chinese medicine ingredients in the traditional Chinese medicine composition of the present invention.

The experimental effect of the present embodiment is obviously superior to the experimental effect of the composition of Example 1. Compared with Example 1, the other conditions are exactly the same, only the fauriella is added, it can be seen that the fauriella has the effect of killing *Trichophyton rubrum* and *Candida albicans*.

Comparative Example 1

Composition

Rhizoma Smilacis Glabrae in 38 parts, *Sophora Flavescens* in 19 parts, Herba Hedyotidis Diffusae in 30 parts, Herba *Taraxaci* in 30 parts, Dysosma Versipellis in 15 parts, Nidus Vespae in 19 parts, Cortex Phellodendri in 30 parts, Fructus Bruceae in 6 parts, Fructus Cnidii in 19 parts, Radix Glycyrrhizae in 7 parts, Flos Lonicerae in 19 parts, Folium *Isatidis* in 19 parts, and 75% ethanol in 1500 parts.

Preparation Method (1) soaking 15 parts of Dysosma Versipellis, 19 parts of Nidus Vespae, 6 parts of Fructus Bruceae, and 19 parts of Flos Lonicerae in 95% ethanol for 10 days, taking out a first supernatant, and ethanol-extracting the first supernatant, and concentrating the supernatant at 65° C., 0.04 MPa to obtain an ethanol extract concentrate;

(2) adding 1920 parts of ionized water into 38 parts of Rhizoma Smilacis Glabrae, 19 parts *Sophora Flavescens*, 30 parts Herba Hedyotidis Diffusae, 30 parts Herba *Taraxaci*, 30 parts of Cortex Phellodendri, 19 parts Fructus Cnidii, 7 parts of Radix Glycyrrhizae, and 19 parts of Folium *Isatidis*, heating and boiling, and taking the filtrate to obtain a water extract was obtained; and (3) mixing the ethanol extract concentrate with the water extract, filtering out a second supernatant, and adding 30% ethanol into the second supernatant to get 750 parts of the traditional Chinese medicine composition.

The Traditional Chinese Medicine Composition of the Present Invention Acts on Cervical HPV Infection and HPV-Induced Cervical Intraepithelial Neoplasia 1. After the confirmation from the hospital outpatients, the test from liquid-based ultrathin (TCT), colposcopy and histopathological examination, the pathological results were confirmed as one of the following conditions: cervical HPV-positive, cervical intraepithelial neoplasia (CIN1, CIN2).

2 Treatment Methods

All of them were treated in non-menstrual period. The sterilized cotton balls with tail line were used to take 1~2 ml of the traditional Chinese medicine composition prepared in Example 1 of the present invention, which was applied to the cervix, and was taken out by the patient for about 1-3 hours, 1 time/d, used 3d for a while, rest for 4d, and used 4 courses of the treatment. Reviewed after deactivation.

3 Efficacy Criteria 3.1 HPV Infection
(1) Cure: HPV DNA review results were negative.
(2) Invalid: HPV DNA review results were positive.

3.2 CIN Cure:
(1) Both TCT and HPV tests were negative. Colposcopy, it was also valid if there was no abnormality under the microscope or confirmed by biopsy to confirm the absence of CIN.
(2) Invalid: pathological diagnosis after biopsy CIN1 or CIN2 remained unchanged.

3.3 The $\chi 2$ test was used for statistical analysis. $P<0.05$ was considered statistically significant.

4. Results

TABLE 9

Traditional Chinese medicine composition of the present invention acts on cervical HPV infection and cervical intraepithelial neoplasia

| Diseases | Number of cases | Valid | Invalid |
| --- | --- | --- | --- |
| Cervical HPV positive | 34 | 18 | 16 |
| C1N1 | 7 | 4 | 3 |
| C1N2 | 4 | 2 | 2 |

Conclusion: The traditional Chinese medicine composition prepared in Example 7 of the present invention has significant treatment effects on cervical HPV infection and HPV-induced cervical intraepithelial neoplasia.

The experimental effect of the present embodiment is obviously lower than the experimental effect of the composition of Example 1. Compared with Example 1, the other conditions are exactly the same, only the radix semiaquilegiae is not added. It can be seen that radix semiaquilegiae has the effect of treating cervical HPV infection and HPV-induced cervical intraepithelial neoplasia.

The foregoing descriptions of specific embodiments of the present invention are presented for purposes of illustration and description. It is not intended to be exhaustive or to limit the invention to the precise form disclosed, and obviously many modifications and variations are possible in light of the above teaching. The exemplary embodiments were chosen and described in order to explain certain principles of the invention and their practical application, to thereby enable others skilled in the art to make and utilize various exemplary embodiments of the present invention, as well as various alternatives and modifications thereof. The invention is to be limited only by the claims provided below and equivalents thereof.

The invention claimed is:

1. A preparation method of a medicine composition, comprising the following steps:
   (1) soaking 13-17 parts of Dysosma Versipellis, 17-21 parts of Nidus Vespae, 4-8 parts of Fructus Bruceae, 17-21 parts of Flos Lonicerae, and 11-15 parts of Radix Semiaquilegiae into 95% ethanol for 8-12 days, taking a first supernatant of soaked solution, extracting using the ethanol, and concentrating the first supernatant at 60-70° C., 0.02-0.05 MPa to obtain an ethanol extract concentrate;
   (2) adding 1400-2500 parts of ionized water to: 36-40 parts of Rhizoma Smilacis Glabrae, 17-21 parts of Sophora Flavescens, 28-32 parts of Herba Hedyotidis Diffusae, 28-32 parts of Herba Taraxaci, 28-32 parts of Cortex Phellodendri, 17-21 parts of Fructus Cnidii, 5-9 parts of Radix Glycyrrhizae, and 17-21 parts of Folium Isatidis, heating and boiling, and taking the filtrate to obtain a water extract; and
   (3) mixing the ethanol extract concentrate with the water extract, filtering out a second supernatant of the mixed solution, and adding 30% ethanol into the second supernatant to get 700-800 parts of the medicine composition.

2. The preparation method according to claim 1, comprising the following steps:
   (1) soaking 15 parts of Dysosma Versipellis, 19 parts of Nidus Vespae, 6 parts of Fructus Bruceae, 19 parts of Flos Lonicerae, and 13 parts of Radix Semiaquilegiae in 95% ethanol for 10 days, taking the first supernatant of the soaked solution, extracting using ethanol, and concentrating the first supernatant at 65° C., 0.04 MPa to obtain an ethanol extract concentrate;
   (2) adding 1920 parts of ionized water to 38 parts of Rhizoma Smilacis Glabrae, 19 parts of Sophora Flavescens, 30 parts of Herba Hedyotidis Diffusae, 30 parts of Herba Taraxaci, 30 parts of Cortex Phellodendri, 19 parts of Fructus Cnidii, 7 parts of Radix Glycyrrhizae, and 19 parts of Folium Isatidis, heating and boiling, and taking out the filtrate to obtain a water extract; and
   (3) mixing the ethanol extract concentrate with the water extract, filtering out a second supernatant, and adding 30% ethanol to get 750 parts of the medicine composition.

3. The method according to claim 1, further comprising measuring specific gravity of the medicine composition by a Baume's specific gravity meter.

4. The preparation method according to claim 1, wherein the specific gravity of the prepared medicine composition is 0.90-1.12.

* * * * *